United States Patent
Wiederin et al.

(10) Patent No.: US 11,498,852 B2
(45) Date of Patent: Nov. 15, 2022

(54) ULTRAPURE WATER GENERATION AND VERIFICATION SYSTEM

(71) Applicant: Elemental Scientific, Inc., Omaha, NE (US)

(72) Inventors: Daniel R. Wiederin, Omaha, NE (US); Mason Spilinek, Omaha, NE (US); Tyler Yost, Omaha, NE (US); Michael Volkmar, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

(21) Appl. No.: 16/560,339

(22) Filed: Sep. 4, 2019

(65) Prior Publication Data
US 2020/0071190 A1    Mar. 5, 2020

Related U.S. Application Data

(60) Provisional application No. 62/727,364, filed on Sep. 5, 2018.

(51) Int. Cl.
*C02F 1/00* (2006.01)
*C02F 1/42* (2006.01)
(Continued)

(52) U.S. Cl.
CPC .............. *C02F 1/008* (2013.01); *C02F 1/001* (2013.01); *C02F 1/42* (2013.01); *G01N 27/06* (2013.01);
(Continued)

(58) Field of Classification Search
CPC .. C02F 1/008; C02F 1/001; C02F 1/42; C02F 1/00; C02F 1/52; C02F 2103/04;
(Continued)

(56) References Cited

U.S. PATENT DOCUMENTS 4,528,093 A * 7/1985 Winer ................. B01D 61/08
                                                            210/257.2
5,476,591 A * 12/1995 Green ................. C02F 1/442
                                                            210/638
(Continued)

FOREIGN PATENT DOCUMENTS

KR    101859135 B1    5/2018
WO     9530471 A1    11/1995

OTHER PUBLICATIONS

International Search Report and Written Opinion for PCT Application No. PCT/US2019/049495, dated Dec. 26, 2019.

*Primary Examiner* — Akash K Varma
(74) *Attorney, Agent, or Firm* — Kevin E. West; Advent, LLP

(57) ABSTRACT

An ultrapure water (UPW) generation and verification system can include a cleaning chemical station, a cleanup column, a conductivity verification station, and a holding reservoir, in fluid communication with one another. The cleaning chemical station can be configured to selectably permit a flow of water to pass therethrough to the cleanup column or to block the flow of water and instead deliver a cleaning chemical to the cleanup column. The conductivity verification station can be configured to selectably perform at least one of the following: permit water to flow from the cleanup column to the holding reservoir; direct fluid to waste; or test the conductivity of the water for a purity level.

9 Claims, 3 Drawing Sheets

(51) Int. Cl.
　　*G01N 27/06*　　　(2006.01)
　　*G01N 33/18*　　　(2006.01)
　　*C02F 103/04*　　　(2006.01)

(52) U.S. Cl.
　　CPC .......... *G01N 33/18* (2013.01); *C02F 2103/04* (2013.01); *C02F 2201/005* (2013.01); *C02F 2209/05* (2013.01); *C02F 2209/40* (2013.01); *C02F 2301/046* (2013.01)

(58) Field of Classification Search
　　CPC ............ C02F 2201/005; C02F 2209/05; C02F 2209/40; C02F 2301/046; C02F 9/00; B01D 35/02; B01D 61/04; G01N 27/06; G01N 33/18
　　USPC ....................................................... 210/96.1
　　See application file for complete search history.

(56) References Cited

U.S. PATENT DOCUMENTS

| | | | | |
|---|---|---|---|---|
| 2005/0211632 | A1* | 9/2005 | Hung | B01D 61/08 210/652 |
| 2009/0039027 | A1* | 2/2009 | Van Niekerk | B01J 41/04 210/673 |

* cited by examiner

ULTRAPURE WATER GENERATION AND VERIFICATION SYSTEM

BACKGROUND

Determination of trace elemental concentrations or amounts in a sample can provide an indication of purity of the sample, or an acceptability of the sample for use as a reagent, reactive component, or the like. For instance, in certain production or manufacturing processes (e.g., mining, metallurgy, semiconductor fabrication, pharmaceutical processing, etc.), the tolerances for impurities can be very strict, for example, on the order of fractions of parts per billion. For example, semiconductor processes can require ultralow detection limits for impurities in process chemicals including, but not limited to, ultrapure water (UPW) for washing wafers, isopropyl alcohol (IPA) for drying wafers, hydrogen peroxide ($H_2O_2$), ammonia solution ($NH_4OH$), and the like. Failure to detect ultralow concentrations of impurities in such process chemicals can ruin a semiconductor wafer, such as by precipitating such impurities out of solution and onto the wafer (e.g., depositing a metallic impurity or other conductivity hazard onto the wafer, such as through precipitation of the impurity out of solution, the wafer acting as a concentrator surface for the impurity, or the like).

SUMMARY

This Summary is provided to introduce a selection of concepts in a simplified form that are further described below in the Detailed Description. This Summary is not intended to identify key and/or essential features of the claimed subject matter. Also, this Summary is not intended to limit the scope of the claimed subject matter in any manner.

Aspects of the disclosure relate to an ultrapure water (UPW) generation and verification system. The system can include a cleaning chemical station, a cleanup column, a conductivity verification station, and a holding reservoir. The cleaning chemical station can be in fluid communication with a particle filter. The cleanup column can be in fluid communication with the cleaning chemical station, the cleaning chemical station configured to selectably permit a flow of water to pass therethrough to the cleanup column or to block the flow of water and instead deliver a cleaning chemical to the cleanup column. The conductivity verification station can be in fluid communication with the cleanup column. The holding reservoir can be in fluid communication with the cleanup column. The conductivity verification station can be configured to selectably perform at least one of the following: permit water to flow from the cleanup column to the holding reservoir; direct fluid to waste; or test the conductivity of the water for a purity level.

DRAWINGS

The Detailed Description is described with reference to the accompanying figures.

DETAILED DESCRIPTION

Overview

Some processing environments have access to a deionized water source but may not have access to sufficient amounts of ultrapure water for various applications where standard deionized water contains too many contaminants (e.g., organic compounds, bacterial contaminants, metallic contaminants, inorganic contaminants, etc.) for the applications as compared to ultrapure water. Additionally, some processing environments lack a way to test the suitability of the water within the processing systems, such as deionized water or ultrapure water provided to the processing environment.

Systems and methods are proposed for generating ultrapure water from a water source and for verifying suitability of the water as an ultrapure water reagent for use in a processing system. When the water does not pass verification, the systems/methods can implement an automatic column cleaning operation (e.g., to regenerate resin within a cleanup column). Example processing systems include, but are not limited to, semiconductor processing applications using ultrapure water and hospital and/or surgical applications requiring ultrapure water.

The present systems and methods have various advantages. The present systems and methods can facilitate the maintenance of a sufficiently pure water supply in an intermittent use/on-demand system (e.g., water retained in a system for an extended period, making it more susceptible to contamination). The present systems and methods can allow for the auto-regeneration of a cleaning column, based, for example, on the purity data collected (e.g., by a resistivity sensor). The present systems can be fluidly coupled to any of a various number of systems in a facility where ultrapure water (e.g., polished water) is needed; or processed and purified water therefrom can be outputted to transportable reservoirs (e.g., tanks or bottles) for transfer to any of various locations where ultrapure water is needed. In an embodiment, the present systems can be coupled with an already available water reservoir (e.g., tank, supply, etc., so long as it is at a lower pressure than the present system). In an embodiment, the system offers a ready supply of water that is sufficiently ultrapure (e.g., "polished") and held at sufficient pressure. In an embodiment, the system can ensure that, even in an intermittent use environment, the water maintained therein can be automatically kept at or below a necessary conductivity threshold (e.g., purity level being inversely related to conductivity) and otherwise capable of cleaning/regenerating itself to maintain such filtration standards.

Example Implementations

Figure 1:
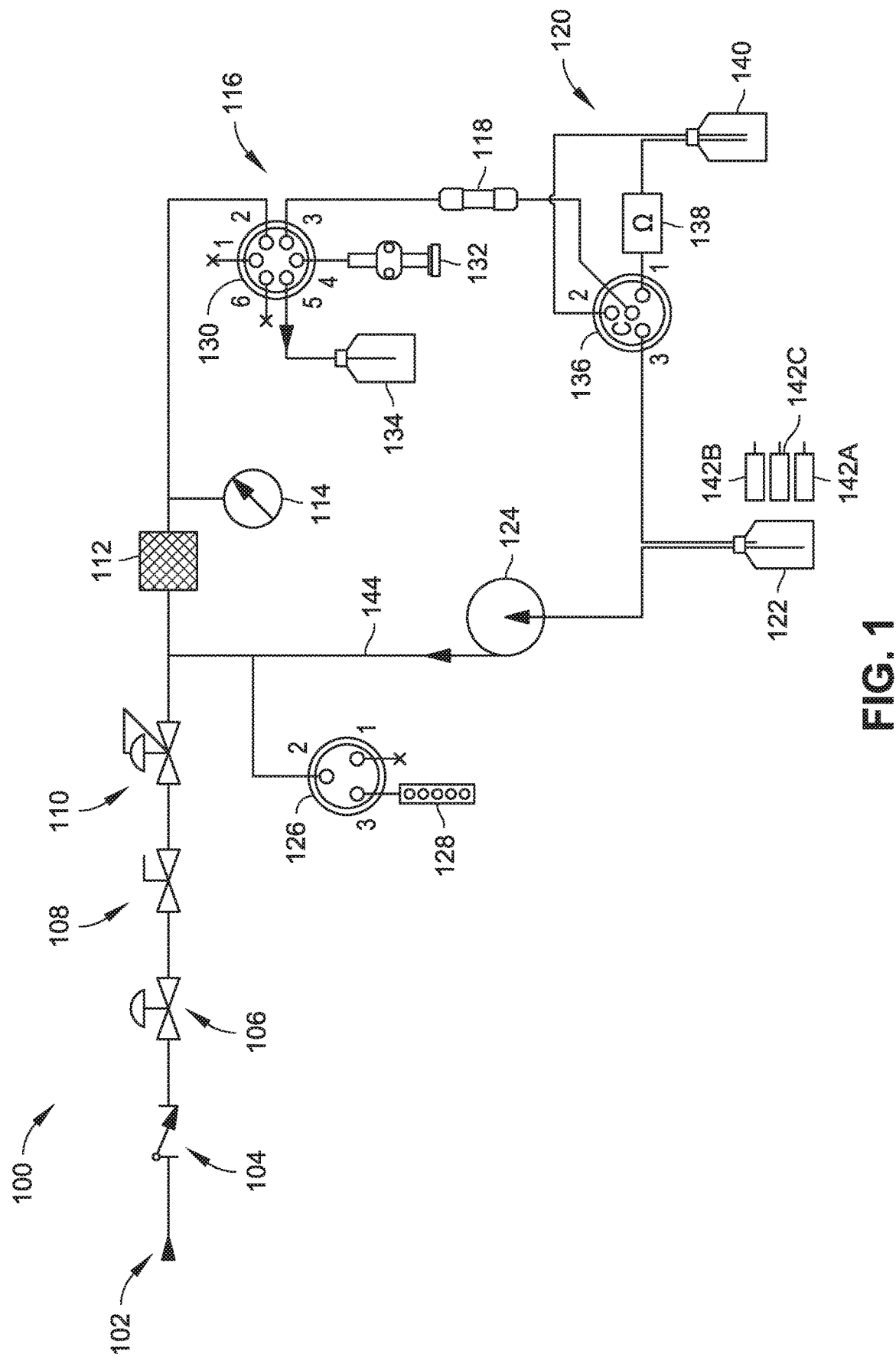
FIG. 1 is a schematic view of an ultrapure water (UPW) generation and verification system, according to an example embodiment of the present disclosure.

FIG. 1 generally illustrates an ultrapure water (UPW) generation and verification system 100, according to an example embodiment of the present disclosure. The system 100 generally can include a water input or inlet 102, a check valve 104, a pneumatic valve 106, a manual valve 108, a pressure regulator 110, a particle filter 112, a pressure sensor or transducer 114, a cleaning or regeneration chemical station 116, a cleaning or cleanup column 118, a purity or conductivity check station (i.e., a water verification station) 120, an ultrapure deionized water (UPDIW) or otherwise ultrapure water holding reservoir 122, a pump (e.g., a centrifugal pump) 124, an outlet control valve (e.g., a 3-port valve) 126, and a system UPDIW or ultrapure water manifold (e.g., a water outlet) 128, with such elements being fluidly interconnected (e.g., via piping, tubing, and/or hoses (not labelled)) as needed to facilitate flow through the system 100. In an embodiment, the water inlet 102, the particle filter 112, the cleaning chemical station 116, the cleanup column 118, the conductivity check station 120, the holding reservoir 122, the pump 124, and the outlet control valve 126 are, in order, located in an upstream-to-downstream fluid flow arrangement relative to one another.

The cleaning chemical station 116 can further include a chemical station multiport valve (e.g., a 6-port valve) 130, a syringe 132, and a chemical source 134 (e.g., an acid; a base; or another chemical suitable for cleaning and regenerating a given cleaning column). In an embodiment, a dilute acid or a dilute base may be used as the regeneration chemical or agent. In an embodiment, the regeneration chemical may be, for example, 10% $HNO_3$ or 5% $NH_3OH$. In an embodiment, a concentrated acid or a concentrated base may be used if first diluted to an appropriate level (e.g., via a dilution pump or syringe), to protect the column(s) while appropriate being appropriate for cleaning them. The conductivity check station 120 can include a check station selection valve (e.g., a 3-port valve) 136, a conductivity sensor (i.e., a purity sensor) 138, and a waste bottle 140, in fluid interconnection. The UPDIW holding reservoir 122 can have a series of water-level sensors 142 (142A-142C, being illustrated) associated therewith. In FIG. 1 "X" locations on select valve sites indicate a blocked or stopped valve position.

The water input 102 of the system 100 can be a source of deionized water (DIW), ultrapure (UP) water, ultrapure deionized water (UPDIW), or other form of water, which may be delivered under pressure. The water input 102 can be coupled, downstream thereof, with one or more valves 104, 106, 108 to regulate the flow of the water into the system 100. For example, a valve (e.g., pneumatic valve 108) to open/close to open/shut off access to the input, a valve (e.g., pressure regulator 110) to regulate a flow rate of the water, a check valve 104 to regulate a direction of flow of the water, a manual valve 108 to manually open/shut flow access (e.g., in case of power outage), or the like can be included. It is to be understood that, in some embodiments, the valves 104, 106, and 108 can be in a different order relative to one another. In an embodiment, the valves 104, 106, and 108, no matter the order relative to one another, are, as a group, located between the water inlet 102 and the particle filter 112, if provided, or, if not, between the water inlet 102 and the cleaning chemical station 116.

Upon passing through the one or more valves 104, 106, 108, the water can be directed through the particle filter 112 (i.e., at a location downstream of the water input 102 and the one or more valves 104, 106, 108) to remove impurities on a size basis. For example, a 0.2-micron filter can be used for the particle filter 112 to remove particulate contaminants, bacterial contaminates, fungal contaminants, or the like. The filtered water can then be directed downstream thereof to the chemical station multiport valve 130, whose flow configuration can depend on the current mode of operation. The system 100 can include, for example, a filtration operation (e.g., at 112), a water verification operation (e.g., at 138), a column cleaning operation (e.g., at 118), and the like. The system 100 can also include a pressure sensor 114 (e.g., coupled between the particle filter 112 and the chemical station multiport valve 130) to monitor a pressure of the water within the system 100, which can indicate blockages within system fluid lines, clogged filters, or the like. In an embodiment, a particle filter 112 may not be provided, with the column cleaning operation serving as the sole mechanism for impurity removal.

During the filtration operation, the filtered water, after having passed through the particle filter 112, is directed through the chemical station multiport valve 130 of the cleaning chemical station 116 to the cleaning column 118 (e.g., water permitted to flow through the valve 130) to remove additional impurities from the filtered water. For example, the cleanup column 118 can include an ion exchange column (e.g., a cation exchange column) including an ion exchange resin therein to remove impurities from the filtered water by binding the impurities to the resin as the water passes through the cleaning column 118. The water leaving the cleanup column 118 can be directed to the check station selection valve 136, which can send the water to the holding reservoir 122 for storage or, periodically, may divert the water for a check of its purity/conductivity (i.e., a water verification operation, to be discussed later).

The holding reservoir 122, located fluidly downstream of the check station selection valve 136, can have one or more water-level sensors 142 associated therewith (located either inside of or proximate to the holding reservoir 122, based on the type of sensor employed). A given water-level sensor 142 may be in the form, for example of a capacitive sensor (as per the illustrated embodiment), an inductive sensor, or an optical sensor in order to determine the level of water within the holding reservoir 122. For example, the holding reservoir 122 can include a first water-level sensor 142A near the bottom of the reservoir to indicate the presence of water within the holding reservoir 122. This level of water can be maintained to ensure sufficient water to prime the pump 124 used to draw water out of the holding reservoir 122 for use by the system 100 and/or for recycling the water through the system 100. A second water-level sensor 142B can be positioned near the top of the holding reservoir 122 to indicate a full status of the holding reservoir 122. A third water-level sensor 142C can be positioned intermediate the first and second water-level sensors 142A, 142B to provide a status of an intermediate water level within the holding reservoir 122. The output from the water-level sensors 142 can be used to control operation of one or more systems components, such as by controlling operation of the pump 124, controlling operation of one or more selection valves (e.g., 106, 110, 126, 130, and/or 136), or the like. For example, the system 100 may direct water to be purified through the system to maintain a presence of fluid at the third water-level sensor 142C (e.g., at an intermediate level within the reservoir), while preventing water from overflowing the holding reservoir 122 (e.g., keeping water below the second water-level sensor 142B). In an embodiment, the water reservoir 122 has a volume that is greater than the remainder of the flow system (excluding any chemical sources or waste tank(s)).

The pump 124 can facilitate removal of water from the holding reservoir 122. For example, the pump 124 can be in the form of a magnetic driven pump or a centrifugal pump. The pump 124 can be configured to supply water to a water outlet (e.g., a water manifold) 128 for providing the water for use in an overall processing system (not shown). The pump 124 can also facilitate water flow through a recycle loop or line 144 to recycle water from the holding reservoir 122 to the particle filter 112. An outlet control valve 126 can control flow of water to the water outlet (i.e., water manifold) 128 and/or to the recycle loop 144. For example, the outlet control valve 126 can divert water away from the water outlet 126 (e.g., to the recycle loop 144) when the water quality does not meet verification standards. The outlet control valve 126 can also facilitate startup procedures for the system 100, where the outlet control valve 126 closes off the water flow to the water outlet 128 during a pump priming operation.

During a pump priming operation, the pump 124 initially is shut off, and water from the water input (e.g., untreated by the system 100) can flow into the recycle line 144 and into the holding reservoir 122 (e.g., in the opposite direction compared to normal flow conditions during operation of the pump 124) to provide a source of fluid to prime the pump 124. For example, in embodiments where the pump 124 is a centrifugal pump, the pump 124 does not operate in an initial dry state. In other words, if there is any moment where air gets into the pump 124, the system 100 can come to a halt and no water can flow. Upon startup, the holding reservoir 122 may be empty or may have an insufficient level of water to prime the pump 124.

During the priming operation, the outlet control valve 126 can close, so none of the unfiltered/non-ultrapure water is able to get to the manifold/water outlet 128. A timer output, for example, can control operation of the pump 124 so that after a certain priming time period elapses (providing sufficient fluid travels from the water inlet 102 to the holding reservoir 122 via the recycle line 144), the pump 124 can turn on to begin functioning. The pump priming operation can occur, for example, on startup of the system 100 or in situations where the holding reservoir 122 contains insufficient fluid to operate the pump 124 (e.g., if emptied or nearly emptied). The pump 124 can output a signal if it is running dry (e.g., via the water level sensor 142A), so the system 100 can monitor for the signal and automatically initiate the pump priming procedure.

During the water verification operation using the conductivity check station 120, the check station selection valve 136 can direct water leaving the cleanup column 118 to a conductivity sensor 138 of the conductivity check station 120 to measure a conductivity of the water. The conductivity of the water is used as a gauge of the purity level of the water, as most, if not all, impurities can be expected to influence the conductivity of the water. The water verification operation can occur according to a system timer (e.g., according to a defined time interval, such as once an hour, once every 15 minutes, once every minute, or the like) or can occur on demand, such as by a user interacting with a user interface to request the water verification. If the conductivity does not exceed a predetermined conductivity threshold (e.g., 18.2 mega-ohms (Mohm)), then the water can be deemed suitable as an ultrapure water reagent, where the check station selection valve 136 can direct the water from the cleanup column 118 to the holding reservoir 122. The system 100 can output an alert (e.g., visual, audio, text to a display) to indicate whether the water passed the conductivity test.

If the conductivity exceeds the predetermined conductivity threshold, then the water is deemed to contain too many impurities to be suitable as an ultrapure water reagent. The system 100 can output an alert (e.g., visual, audio, text to a display) to indicate that the water failed the conductivity test. Failure of the conductivity test can provide an indication that the cleanup column 118 is saturated and should be regenerated, whereby the system 100 can automatically proceed to the column cleaning operation. For instance, a system controller (not shown) can receive an output from the conductivity sensor 138 and manipulate the system valves (e.g., 106, 110, 126, 130, and/or 136) and pump (e.g., 124) to proceed between the various system operations automatically. In an embodiment, the use of a conductivity sensor 138 that is in the form of an inline sensor coupled between the holding reservoir 122 and the cleanup column 118 (e.g., without a selection valve diverting water from the cleanup column to a separate flow pathway) is considered within the scope of the present disclosure.

During the column cleaning operation using the cleaning chemical station 116, the chemical station multiport valve 130 of the cleaning chemical station 116 can direct the cleaning/regeneration chemical from the chemical source 134 (e.g., introduced via operation of a syringe pump 132) to the cleanup column 118. In an embodiment, the chemical used may be a nitric chemical (e.g., 70% nitric, by weight). The provision of the chemical or other suitable chemical to the cleanup column 118 can regenerate the resin (not labelled) contained within the cleanup column 118, whereby impurities are retained by the chemical or other cleaning/regeneration chemical flowing through the cleanup column 118, thereby removing the impurities from the cleanup column 118. The chemical removed from the cleanup column 118 can be directed to the waste bottle 140 of the conductivity check station 120, without interacting with the conductivity sensor 138 or other components downstream from the cleanup column 118, such as the holding reservoir 122. Water can be rinsed through the cleanup column 118 and directed to the waste bottle 140 to remove any residual regeneration chemical within the cleanup column 118 following the column cleaning operation. In an embodiment, the cleaning/regeneration chemical can be drawn into the system via the chemical station multiport valve 130 or a manifold (not shown) using the syringe pump 132. In an embodiment, the system can instead use the pump 124 to draw the cleaning/regeneration chemical through the chemical station multiport valve 130 or a manifold (which may allow for the system to be designed without a syringe pump).

Further, the opening/closing of the outlet control valve 126 to the water outlet 128 can be controlled, in part, based on an output from the conductivity or purity sensor 138. For example, when the water quality does not meet standards, the outlet control valve 126 can be closed to prevent water from being accessible to the water manifold 128 for use in the overall processing system. When the water quality again meets standards, the outlet control valve 126 can be opened to permit access of the water in/from the holding reservoir 122 to the water outlet 128 (e.g., via pump operation).

Figure 2:
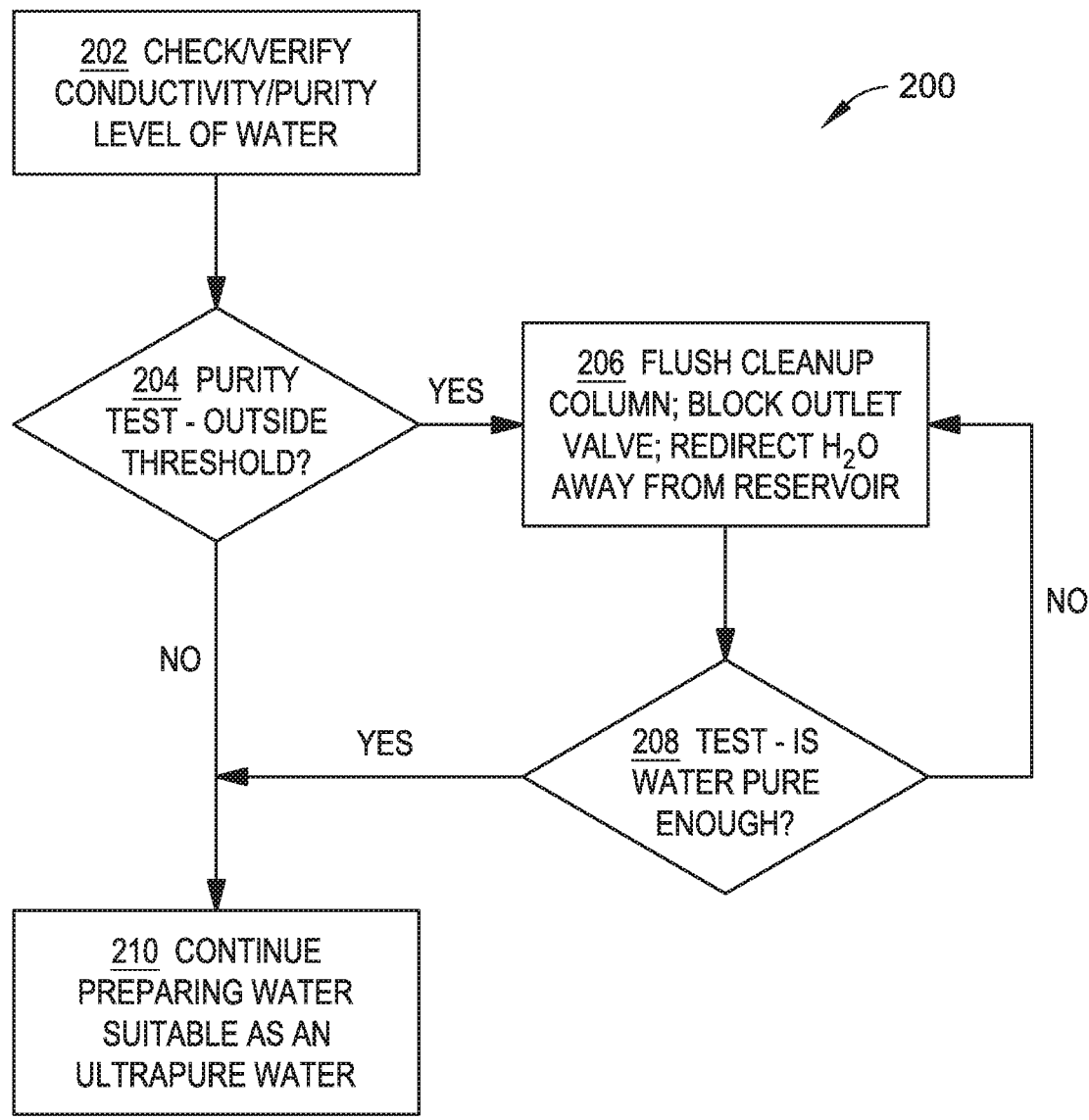
FIG. 2 is a flowchart of the water verification operation associated with the use of the UPW generation and verification system of FIG. 1.

An example embodiment of the verification testing and column cleaning protocol 200 is summarized in FIG. 2. At step 202, the conductivity/purity level of the water is checked or verified. Step 202 has an associated decision block 204, determining whether the water conductivity requires a flush of the cleanup column with a cleaning chemical (i.e., does the conductivity test fail to meet requirements or is the conductivity outside an acceptable threshold value or range?). If "yes" and a flush is needed (i.e., to rejuvenate the resin of the cleanup column 118), the next step in the process is the step 206 of flushing the cleanup column 118 with a regeneration chemical, closing of the outlet valve 126, and redirecting flow away from the holding reservoir 122 (e.g., direct to waste or through the conductivity sensor) via the check station selection valve 136. An chemical flush (step 206) can be followed by another water conductivity test (step 208) upon flowing water through the cleanup column 118, a water flush to remove any residual chemical without specifically testing the water for purity, and/or recycling (e.g., running it all back through the cleanup column 118) or dumping to waste any water already in the holding reservoir 122 (e.g., if there is doubt as to the purity level of the water contained therein—that choice may be based, for example, on the time between tests, the purity level test score that prompted the flush, etc.).

If the result of the conductivity test 206 is negative (i.e., not pure enough), then the flush cleanup step 204 is repeated, with another water conductivity test 206 to be performed thereafter. If, however, the result of the conductivity test 206 is positive (i.e., sufficient purity level), then it is possible to proceed to step 208 of continuing to prepare water suitable as an ultrapure water (e.g., process through cleanup column 118 and be allowed to flow to the holding reservoir 122). Likewise, coming out of the decision block 202, if the measured water conductivity is such that no flush of the cleanup column 118 is needed (i.e., water is sufficiently pure upon exiting the cleanup column), then it is possible to proceed directly to step 208, as well. Thus, the cleaning chemical station 116 can be configured to selectably permit water to pass therethrough to the cleanup column 118 or to block the flow of water and instead deliver a cleaning chemical to the cleanup column 118. Further, the water verification station 120 can be configured selectably to permit filtered water to pass therethrough to the holding reservoir 122 or to redirect the fluid (e.g., chemical or water), either directly to the waste bottle 140 (e.g., in the case of the chemical wash or, if desired, a water flush performed after an chemical wash of the cleanup column 118) or through the conductivity sensor 138 before reaching the waste bottle 140 (as part of a water verification test for purity). It is to be understood that while the waste receiving location is shown as a waste bottle 140, the waste receiving location could be, for example, a waste delivery line or another type of reservoir (e.g., not necessarily a bottle).

Figure 3:
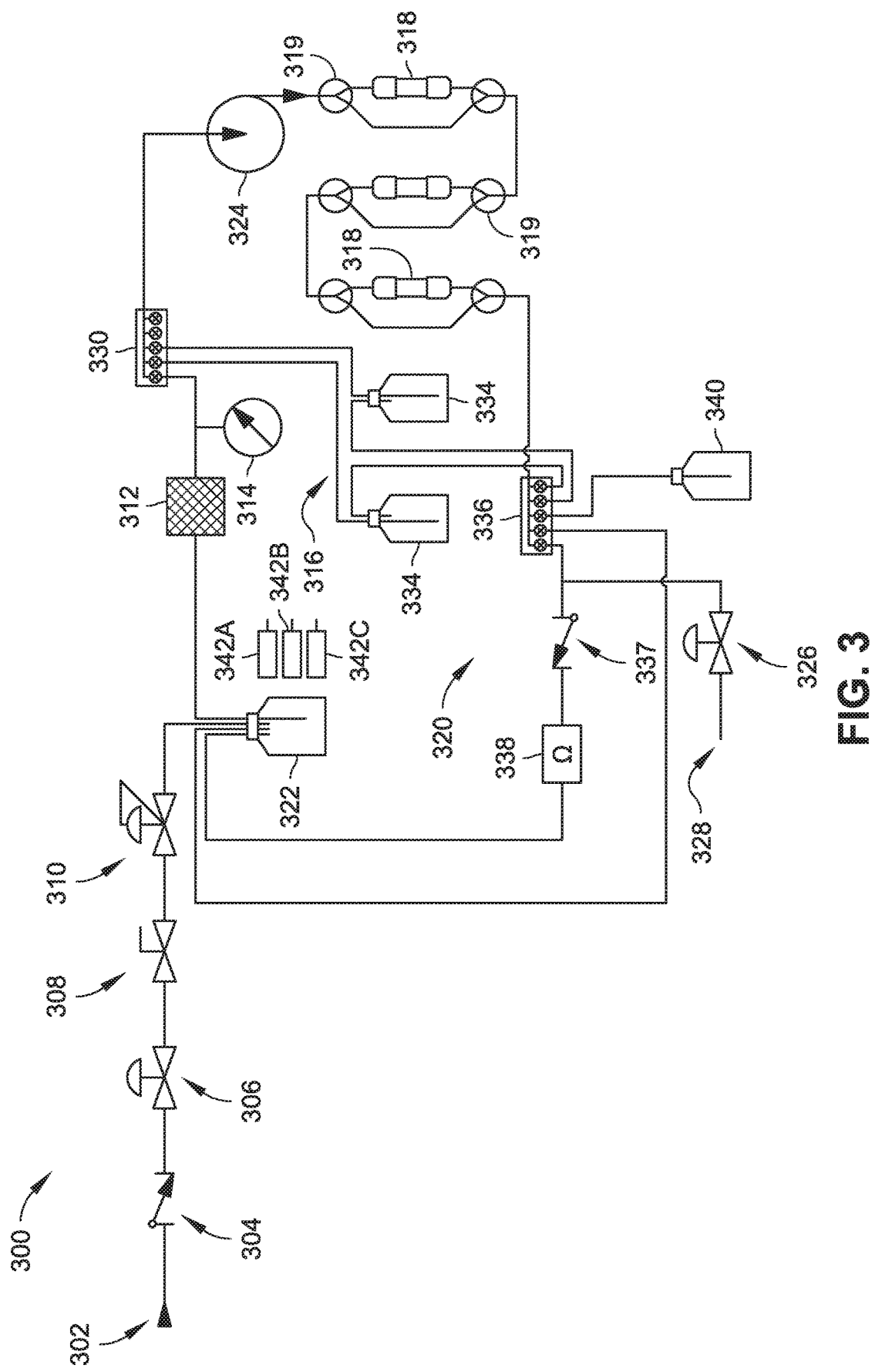
FIG. 3 is a schematic view of an ultrapure water (UPW) generation and verification system, according to an example embodiment of the present disclosure.

FIG. 3 generally illustrates an ultrapure water (UPW) generation and verification system 300, according to an example embodiment of the present disclosure. The system 300 generally can include a water input or inlet 302, a check valve 304, a pneumatic valve 306, a manual valve 308, a pressure regulator 310, a particle filter 312, a pressure sensor or transducer 314, a cleaning or regeneration chemical station 316, at least one cleaning or cleanup column 318 (three of which are shown), a plurality of 3-way valves 319 (e.g., at entry and exit points at each cleaning column 318), a purity or conductivity check station (i.e., a water verification station) 320, an ultrapure deionized water (UPDIW) or otherwise ultrapure water holding reservoir 322, a pump (e.g., a centrifugal pump) 324, an outlet control valve (e.g., a pneumatic valve) 326, and a system UPDIW or ultrapure water outlet 328 (e.g., an outlet manifold capable of directing water to multiple locations; or a direct line outlet), with such elements being fluidly interconnected (e.g., via piping, tubing, and/or hoses (not labelled)) as needed to facilitate flow through the system 300.

The cleaning chemical station 316 can further include a chemical station manifold 330 (serving a similar function and purpose as a chemical station multiport valve 130 but with a multi-valve manifold unit) and at least one chemical source 334 (e.g., an acid; a base; or another chemical suitable for cleaning and regenerating a given cleaning column), of which two such chemical sources 334 are illustrated in the form of "REGEN BOTTLE #1" and "REGEN BOTTLE #2." The conductivity check station 320 can include a check station selection manifold 336 (serving a similar function and purpose as a check station selection valve 136 but in the form of a multi-valve manifold), a conductivity line check valve 337, and a conductivity sensor (i.e., a purity sensor) 338, and a waste bottle 340, in fluid interconnection. A waste bottle 340 can be in selective fluid connection with the main flow path, for example, via the check station selection manifold 336. The UPDIW holding reservoir 322 can have a series of water-level sensors 342 (342A-342C, being illustrated) associated therewith. In FIG. 3, "X" locations on select manifold sites can indicate a blocked or stopped valve position, positions which may be selectably opened to achieve a desired flow.

Like part numbers (e.g., manual valves 108, 308) to those used for the embodiment associated with FIG. 1 can be expected to have similar features and functionality, unless otherwise described herein. As such, the description of the embodiment of FIG. 3 generally focuses on those features that distinguish it from the embodiment associated with FIGS. 1 and 2.

There are multiple features of the system 300 that differ, to at least some degree, from the system 100. First, the chemical station manifold 330 can be used to select the cleaning chemical or solution to be pulled from one of the available chemical sources 334 (e.g., illustrated as "REGEN BOTTLE #1" and "REGEN BOTTLE #2"). Instead of employing a syringe pump 132 as with the system 100, the desired cleaning chemical to be used to regenerate one or more of the cleaning columns 318 can be drawn through the chemical station manifold 330 into the flow path ahead of any of the cleaning columns 318. In an embodiment, the pump 324 can be located in the main fluid line between the chemical station manifold 330 and the set of cleaning columns 318, to promote suction regeneration chemicals and/or ultrapure water toward the cleaning columns 318. Such pump positioning can help ensure that the fluids reach the cleaning columns 318 at near maximum pressure to promote filtration or filter cleaning, as the case may be). The valves (not individually labelled) that are incorporated in the chemical station manifold 330 can be selectably oriented so that water may be drawn from the ultrapure water holding reservoir 322 and/or a regeneration chemical may be drawn from one of the chemical sources 334. It is to be understood that one or more than two chemical sources 334 may be available and that the chemical station manifold 330 may include an appropriate number of valves to facilitate delivery from the main flow line (e.g., from the water source 322) and from any of the available chemical sources 334.

Further, the system 300 can have a plurality of 3-way valves 319 positioned respectively positioned before or after a given cleaning column 318. Such 3-way valves 319 can together be configured to selectably permit flow-through or bypass of any of the cleaning columns 318. In some embodiments, different cleaning columns 318 may be employed to permit specialized cleaning of different classes of ions or impurities from the water. In some embodiments, at least two redundant cleaning columns 318 may be employed, for example, to delay the time between regeneration steps (i.e., able to use a first and then a second column before the need to regenerate). In an embodiment, a respective pair of 3-way valves 319 can be associated with a corresponding cleaning column 318 (e.g., one before and one after). In an embodiment, a given 3-way valve 319 can be a pneumatic valve with one inlet and two outlets, with the two outlets being selectable therebetween. The presence of the two outlets can allow the choice to either bypass a cleaning column 318 or enter a cleaning column 318 with a cleaning solution or with ultrapure water, as desired. In some embodiments, it can be desirable to use different regeneration/cleaning chemicals for some or all the cleaning columns 318 (e.g., the cores of the cleaning columns 318 may not all have the same composition and thus may be best regenerated using different chemicals/solutions).

The conductivity check station 320 has various features which may differ from the conductivity check station 120. The check station selection manifold 336 is configured to select the flow destination (e.g., of the water or cleaning solution) after the fluid being conveyed passes beyond the one or more cleaning columns 318. Using the check station selection manifold 336, the solution and/or water can be directed to a chosen chemical source 334 (e.g., a bottle of a regeneration solution), the waste bottle 340, or the ultrapure water holding reservoir 322. In an embodiment, the check station selection manifold 336 can be selectably activated to cause a flow to bypass or to enter the flow path including the conductivity sensor 338. The flow path including the conductivity sensor 338 includes the conductivity line check valve 337 positioned between the check station selection manifold 336 and the conductivity sensor 338 to ensure potentially contaminated water from the ultrapure water reservoir 322 and/or the line including the conductivity sensor 338 cannot be inadvertently pulled toward the ultrapure water outlet 328. In the embodiment shown in FIG. 3, the flow through the line including the conductivity sensor 338 may include a three-way valve or manifold (neither shown) is directed to the ultrapure water reservoir 322. Alternatively, that line, after the conductivity sensor, may include a three-way valve or manifold and related flow paths (neither option shown) to allow the flow through that line to be selectably directed to one of the ultrapure water reservoir 322 or the waste bottle 340 (note that such a feature could be incorporated in system 100 instead of directing the flow solely to waste). Yet further alternatively, the flow beyond the conductivity sensor 338 may be directed solely to the waste bottle 340 (e.g., as is the case in system 100).

The outlet control valve 326 can proceed the ultrapure water outlet 328 in the system flow path. The outlet control valve 326 can be a pneumatic valve. The use of a pneumatic valve as the outlet control valve 326 can permit automatic shut-off of a flow to the outlet 328 if conductivity of the water is determined to fall below a chosen set value or threshold. As such, controlling of the outlet control valve 326 in this manner achieves the same basic effect as did the operation of the outlet control valve 126 in the system 100.

System 300 can facilitate column regeneration. With respect to column regeneration, the chemical station manifold 330 and the check station selection manifold 336 can be set to permit a desired cleaning solution to recirculate through one or more desired cleaning columns 318. After a certain time of recirculation, the chemical station manifold 330 can be set to select flow from the ultrapure water holding reservoir 322, and the check station selection manifold 336 can direct the flow to the waste (e.g., the waste bottle 340). As such, in that arrangement, ultrapure water is flushed for a certain time through the system through the particle filter 312 and one or more of the cleanup columns 318, as desired for cleaning and/or regeneration, and dumped to waste, before the return is switched back to the reservoir 322. As part of switching the return toward the reservoir 322, the conductivity can be monitored at the conductivity sensor 338. If the conductivity is found to be unacceptable, the system 300 can be switched back to the "flush mode" (e.g., rinse with ultrapure water and dumped to waste) for a certain time (e.g., the time length may be tied to the conductivity—the higher the conductivity, the longer the flush) and the conductivity then rechecked by channeling the fluid toward the conductivity sensor 338 and the reservoir 322.

The system 300 can offer certain advantages. The system 300 can permit continuous monitoring of the conductivity of the output to the ultrapure water reservoir 322, yielding a much quicker response time to any contamination events. By directing water monitored for conductivity to the ultrapure water reservoir 322, the waste volume can be reduced (i.e., water that previously was able to pass the conductivity test was nonetheless directed to waste). Through system control and use of the check station selection manifold 336, the amount of contaminated water reaching the ultrapure water reservoir 322 after a failed test at the conductivity sensor 338 can be minimized (i.e., the fraction of contaminated water combining with the ultrapure water can be relatively small, particularly depending on the size of the ultrapure water reservoir 322). Thus, the benefit of real time conductivity measurement and decreased waste volume can outweigh the small additional cleaning/filtration load on the respective columns.

In an embodiment, the water in the ultrapure water reservoir 322 need not be at 18.2 mega-ohms (i.e., the level of purity, while desirable, is not as critical in the arrangement per the system 300). That is, even if the water in the ultrapure water reservoir 322 has a conductivity above 18.2 mega-ohms (e.g., contaminants introduced, per a failed conductivity test), any water from the reservoir 322 must yet again pass through both the particle filter 312 and at least one of the cleaning columns 318 before reaching the ultrapure water outlet 328. As such, upon exiting the system, presuming column regeneration is not needed, the water may be sufficiently pure for release to other systems requiring ultrapure water, even under that scenario. Additionally, since all water under this scenario is to be directed through a full filtration cycle before exiting the system to other locations for use, in some embodiments, it can be possible to not have a section of tubing/flow path prior to the outlet valve 326 that necessarily must be kept clean at all times. In an embodiment, the section of the flow path after the columns 318 to the outlet valve 326 needs to be kept at a clean level of 18.2 mega-ohms or lower when the system 300 is not undergoing regeneration or post-regeneration flush.

In some embodiments, the systems 100 and/or 300 or variants thereof can be used as an offline water cleaning (e.g., water polishing, in the sense that the water is being cleaned and/or scrubbed of contaminants) station. In such cases, it can be desirable to get and/or maintain the reservoir 122, 322 as clean as possible. Under those circumstances, it can be best to direct the flow stream traveling through the conductivity sensor 138, 338 directly to waste, to avoid adding any contaminants to the reservoir 122, 322.

The pressure sensor 114, 314, the conductivity sensor 138, 338, the water level sensors 142, 342, the system valves (e.g., 106/306, 110/310, 126/326, 130/330, and/or 136/336), the syringe 132, 332, and pump 124, 324, along with any other elements of the system 100, 300 capable of being electrically or electronically linked, can be communicatively connected (e.g., via wired or wireless communication) to a system controller (not shown) for the system 100, 300, with the system controller, at least in part, configured to automatically facilitate the operations discussed above. The system controller may further be in communication with one or more system inputs (e.g., touchscreen, keypad, keyboard, etc.) and/or one or more system outputs (e.g., visual display or audio or visual signal). It is to be understood that other sensors (not shown) may be incorporated within the system 100, 300, such as an chemical flow or level detection sensor for detecting when more chemical is needed and/or a waste bottle level sensor for detecting when the waste bottle contents need to be emptied. For example, a predetermined drop in pressure registered by the pressure sensor or transducer 114, 314 may be used as an indicator that the particle filter 112, 312 needs to be cleaned and/or changed.

In embodiments, the system controller can include a processor, a memory, and a communications interface. The processor provides processing functionality for at least the controller and can include any number of processors, microcontrollers, circuitry, field programmable gate array (FPGA) or other processing systems, and resident or external memory for storing data, executable code, and other information accessed or generated by the controller. The processor can execute one or more software programs embodied in a non-transitory computer readable medium that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The memory can be an example of tangible, computer-readable storage medium that provides storage functionality to store various data and or program code associated with operation of the controller, such as software programs and/or code segments, or other data to instruct the processor, and possibly other components of the system 100, to perform the functionality described herein. Thus, the memory can store data, such as a program of instructions for operating the system 100 (including its components), and so forth. It should be noted that while a single memory is described, a wide variety of types and combinations of memory (e.g., tangible, non-transitory memory) can be employed. The memory can be integral with the processor, can comprise stand-alone memory, or can be a combination of both.

Some examples of the memory can include removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, remove (e.g., server and/or cloud) memory, and so forth. In implementations, memory can include removable integrated circuit card (ICC) memory, such as memory provided by a subscriber identity module (SIM) card, a universal subscriber identity module (USIM) card, a universal integrated circuit card (UICC), and so on.

The communications interface can be operatively configured to communicate with components of the system 100, 300. For example, the communications interface can be configured to transmit data for storage by the system 100, 300, retrieve data from storage in the system 100, and so forth. The communications interface can also be communicatively coupled with the processor to facilitate data transfer between components of the system 100, 300 and the processor. It should be noted that while the communications interface is described as a component of controller, one or more components of the communications interface can be implemented as external components communicatively coupled to the system 100, 300 or components thereof via a wired and/or wireless connection. The system 100, 300 or components thereof can also include and/or connect to one or more input/output (I/O) devices (e.g., via the communications interface), such as a display, a mouse, a touchpad, a touchscreen, a keyboard, a microphone (e.g., for voice commands) and so on.

The communications interface and/or the processor can be configured to communicate with a variety of different networks, such as a wide-area cellular telephone network, such as a cellular network, a 3G cellular network, a 4G cellular network, a 5G cellular network, or a global system for mobile communications (GSM) network; a wireless computer communications network, such as a WiFi network (e.g., a wireless local area network (WLAN) operated using IEEE 802.11 network standards); an ad-hoc wireless network, an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface can be configured to communicate with a single network or multiple networks across different access points. In a specific embodiment, a communications interface can transmit information from the controller to an external device (e.g., a cell phone, a computer connected to a WiFi network, cloud storage, etc.). In another specific embodiment, a communications interface can receive information from an external device (e.g., a cell phone, a computer connected to a WiFi network, cloud storage, etc.).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. For example, where appropriate and not necessarily precluded, the features discussed with respect to systems 100 and 300 may be mixed and matched.

What is claimed is:

1. An ultrapure water (UPW) generation and verification system comprising:
   at least one cleanup column configured to remove impurities from a flow of water therethrough;
   a holding reservoir in selectable fluid communication with the at least one cleanup column; and
   a conductivity verification station in direct fluid communication with the at least one cleanup column, the holding reservoir, and a waste reservoir, the conductivity verification station located between the at least one cleanup column and the holding reservoir, the conductivity verification station configured to selectably perform at least the following steps: direct fluid to the waste reservoir; or test a conductivity of the flow of water for a purity level.

2. The ultrapure water (UPW) generation and verification system of claim 1, further comprising a cleaning chemical station in fluid communication with the at least one cleanup column and located upstream of the at least one cleanup column, the cleaning chemical station configured to selectably permit the flow of water to pass therethrough to the at least one cleanup column or to block the flow of water and instead deliver a cleaning chemical to the at least one cleanup column.

3. The ultrapure water (UPW) generation and verification system of claim 1, further comprising a particle filter positioned upstream of and in fluid communication with the at least one cleanup column.

4. The ultrapure water (UPW) generation and verification system of claim 1, further comprising a water input to provide the flow of water to be directed to the at least one cleanup column and further comprising one or more valves in fluid communication with the water input to regulate the flow of water into the ultrapure water (UPW) generation and verification system.

5. The ultrapure water (UPW) generation and verification system of claim 1, wherein the at least one cleanup column includes an ion exchange resin therein.

6. The ultrapure water (UPW) generation and verification system of claim 1, wherein the conductivity verification station further comprises a water purity sensor configured to determine the purity level of the water based upon the conductivity thereof, the water configured to be directed through the water purity sensor to determine the purity level of the water.

7. The ultrapure water (UPW) generation and verification system of claim 6, wherein the conductivity verification station is configured to direct the water flowing through the water purity sensor to the holding reservoir.

8. The ultrapure water (UPW) generation and verification system of claim 1, further comprising a pump configured to facilitate removing the water from the holding reservoir and directing the water to at least one of a water outlet or a recycle loop.

9. The ultrapure water (UPW) generation and verification system of claim 2, further comprising a pump located between the cleaning chemical station and the at least one cleanup column.

\* \* \* \* \*